United States Patent [19]

Mossa

[11] Patent Number: 4,740,521
[45] Date of Patent: Apr. 26, 1988

[54] SAUDIN, A NOVEL HYPOGLYCEMIC AGENT

[75] Inventor: Jaber S. Mossa, Riyadh, Saudi Arabia

[73] Assignees: Purdue Research Foundation, West Lafayette, Ind.; King Saud University, Riyadh, Saudi Arabia

[21] Appl. No.: 823,667

[22] Filed: Jan. 29, 1986

Related U.S. Application Data

[63] Continuation-in-part of Ser. No. 583,371, Feb. 21, 1984, abandoned.

[51] Int. Cl.$^4$ .................. A61K 31/365; C07D 493/22
[52] U.S. Cl. .................. 514/453; 549/275; 549/276
[58] Field of Search ............... 549/275, 276; 514/453

*Primary Examiner*—Jane T. Fan

[57] ABSTRACT

Saudin, a novel terpenoid substance having hypoglycemic properties, isolated from the plant *Cluytia richardiana* L. Euphorbiaceae, and a method for lowering blood sugar by injection thereof into the body.

5 Claims, 1 Drawing Sheet

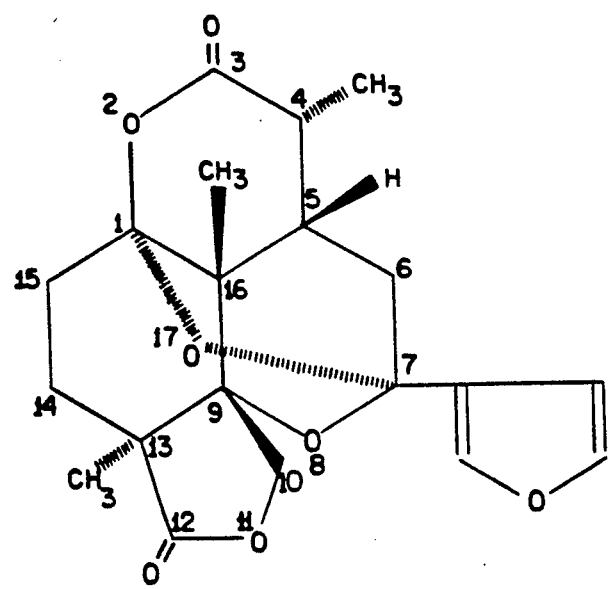
SAUDIN

SAUDIN, A NOVEL HYPOGLYCEMIC AGENT

This application is a continuation-in-part of U.S. application Ser. No. 06/583,371, filed Feb. 21, 1984 now abandoned.

This invention relates to the control of hyperglycemia. More particularly, it relates to a novel hypoglycemic substance isolated from a complex naturally occuring mixture, and to the use thereof in the treatment of diabetes mellitus.

The novel substance of the present invention has been given the common or generic name "saudin." It is a terpenoid substance having the chemical structure shown on the accompanying drawing, and the full chemical name (according to the I.U.P.A.C. system of nomenclature) of $(-)$-$(1R,4R,5S,7R,9S,13S,16R)$ -7-(3-furanyl)-4,13,16-trimethyl-2,8,11,17-tetraoxapentacyclo $[7.6.1.1^{1,7}.0^{5,16}.0^{9,13}]$heptadeca-3,12-dione.

Saudin occurs naturally in a plant, *Cluytia richardiana* L. Euphorbiaceae, found growing widely and extensively along the mountainous regions (3,000 to 4,000 feet above sea level) of western and southern Saudi Arabia. The plant normally grows to a height of about one meter, and is characterized by an erect stem and simple leaves, growing alternately. The younger branches are green, while older stems are dark reddish brown in color. The foliage is toxic to livestock.

Saudin occurs principally in the foliage of *Cluytia richardiana*, preferably collected during the flowering season. The leaves are separated from the stems, dried in the shade, powdered, and extracted with a hydrocarbon solvent such as a light petroleum distillate fraction, petroleum ether being the preferred extractant. The extract is adsorbed on silica gel in a chromatographic column and fractionally eluted through silica gel with ethyl acetate-hexane (1:1 by volume), the fractions being readily identified and segregated by color. Saudin is found in the fifth fraction, orange-red in color, from which it is readily obtained in the form of white crystals, m.p. 202° C. Details of the several fractions contained in the extract are given below in the operating example.

When administered by injection, saudin produces a significant hypoglycemic effect in animals at doses above about 10 mg/kg. For the control of hyperglycemia, a dose between about 25 and about 110 mg/kg is effective, when administered at intervals of about 2 to about 12 hours in a tissue-compatible liquid. Normal saline solution is a suitable solvent diluent, or alternatively aqueous carboxymethylcellulose.

The following example is illustrative of the invention and of the best mode of isolating and utilizing the novel substance provided thereby.

EXAMPLE

The plant, *Cluytia richardiana*, was authenticated and collected during flowering season, and the leaves were separated, dried in open air in the shade, and ground to a powder. One kilogram of the powdered material was continuously extracted with petroleum ether (boiling range, 60°–80° C.) for 20 hours in a Soxhlet extractor. A test confirmed the presence of hypoglycemic activity in the resulting extract.

The solid residue from the extraction ("marc") was re-extracted successively with chloroform, then with methanol. In neither case was any hypoglycemic activity found in the extract.

The petroleum ether extract was subjected to a preliminary examination by thin-layer chromatography on silica gel, using ethyl acetate-hexane (1:1 by volume) for the mobile phase and a spray of anisaldehyde/sulfuric acid for visualization. The chromatogram showed four well-separated spots.

The entire petroleum ether extract was then adsorbed on 50 g of silica gel 60 (0.05–0.20 mm/70–270 mesh) and developed on a column one meter in length by 5 cm in diameter, packed with silica gel of the same grade. The developing solvent was ethyl acetate-hexane (1:1 by volume). The fractions were readily separable by color, and were concentrated to recover any dissolved solids. The results were as follows:

Fraction 1: 100 ml, green-yellow, giving (on being concentrated) 8 g of a white, waxy precipitate, m.p. 60° C.

Fraction 2: 150 ml, yellow, giving one gram of a white precipitate, m.p. 60° C.

Fraction 3: 100 ml, red, giving a reddish semiliquid, possibly anthocyanins.

Fraction 4: 200 ml, yellow, giving 59 gm of small, light crystals, m.p. 265° C.

Fraction 5: 250 ml, orange-red, giving 600 mg of white crystals, m.p. 202° C. This compound was saudin.

Fraction 6: 100 ml, yellow, giving 250 mg of fine yellow crystals, m.p. 223°–225° C.

Fraction 7: 100 ml, orange to yellow, giving 78 mg of white quasi-crystalline solid, m.p. 275° C.

Fraction 8: 300 ml, yellow, giving a yellow semiliquid.

Fraction 9: 100 ml, orange, giving an orange semiliquid.

Fraction 10: 100 ml, yellow, giving 20 g of a very light white precipitate.

Fraction 11: 200 ml, pale yellow, giving no residue on concentration.

The solid obtained from Fraction 5, on being concentrated and crystallized from ether acetate/carbon tetrachloride was unchanged in melting point (202° C.); MS, m/z 374.1376, calc. for $C_{20}H_{22}O_7$, 374.1365; UV, $\lambda_{max}=212$ nm ($\epsilon=3300$), EtOH. These results are consistent with the structure of saudin, shown in the accompanying drawing, that was determined by x-ray crystallography.

When suspended in carboxymethylcellulose (1.5%) and injected i.p. into mice according to the method of Miller and Tainter, *Proc. Soc. Exp. Biol. Med.*, 57, 261 (1944), saudin was found to have a median lethal dose (LD50) of $500\pm15.79$ mg/kg, closely comparable to tolbutamide, $490\pm12.9$ mg/kg, when similarly tested.

The hypoglycemic effect of saudin was demonstrated by the following tests in mice.

METHODS

Male albino rats weighing from 100–150 gm were divided into groups each comprised from 7–8 rats. The groups were sub-divided into subgroups of non-fasted rats and fasted rats which did not receive food for 20 hours before taking blood samples. Non-fasted and fasted rats were either non-alloxanized or injected I.V. with alloxan at a dose of 40 mg/kg two days before administration of saudin. Saudin was injected I.P. in the experiment groups in a suspension form containing 0.5% carboxymethylcellulose (CMC). Control groups received I.P. injection of 0.5% CMD at a dose not exceeding 1 ml/100 gm (Maximum volume used to suspend saudin). Blood samples were taken and the plasma glucose level was estimated as indicated in the results. The method used for glucose estimation was similar to that used by Free et al., *Advances in Clinical Chemistry*, E. H. Sobotaka and C. P. Steward (eds.), Academic Press, New York, 6, p. 67 (1973).

RESULTS

Table 1 shows that saudin at a dose of 40 mg/kg I.P. induced a significant hypoglycemic effect in non-alloxanized fed rats two hours after injection. Saudin did not alter the plasma glucose levels in fasted alloxanized and non-alloxanized rats nor in fed alloxanized rats (Table 2).

TABLE 1

Effect of saudin on the plasma glucose level of non-fasted rats in response to I.P. injection of 40 mg/kg. Blood samples were taken at 1 h intervals in heparinized tubes and plasma was separated for glucose estimation.

| Group | Plasma glucose level, mg/dl, S.E. | | | | |
|---|---|---|---|---|---|
| | 0 h | 1 h | 2 h | 3 h | 4 h |
| Control (1 ml/100 gm C.M.C. I.P.) | 113.63 ± 7.50 | 115.25 ± 5.78 | 126.75 ± 4.62 | 105.00 ± 3.23 | 104.73 ± 4.11 |
| Saudin (40 mg/kg I.P.) | 109.75 ± 3.05 | 127.86 ± 4.45 | 107.00 ± 2.31* | 97.00 ± 3.78 | 98.00 ± 4.81 |

*Significant difference from the corresponding control value at $P < 0.01$.

TABLE 2

Effect of saudin on the plasma glucose level of alloxanized and non-alloxanized rats either fasted or non-fasted. Blood samples were taken 2 hours after saudin injection in tubes containing heparin. Plasma was separated for glucose estimation.

| Plasma glucose level, mg/dl, S.E. | | | | | | | |
|---|---|---|---|---|---|---|---|
| Non-alloxanized rats | | | | Alloxanized rats (40 mg/kg alloxan I.V. 2 days before saudin injection) | | | |
| Fasted | | Non-fasted | | Fasted | | Non-fasted | |
| Control | Exp. | Control | Exp. | Control | Exp. | Control | Exp. |
| 81.14 ± 4.31 | 79.86 ± 3.05 | 132.14 ± 3.82 | 111.85 ± 2.22* | 116.66 ± 6.64 | 103.5 ± 4.45 | 141.2 ± 3.43 | 142.8 ± 10.78 |

*Significant difference from the control value at $P < 0.01$.

In further tests, it was confirmed that saudin (unlike tolbutamide) does not produce a hypoglycemic effect in alloxanized mice (i.e., mice in which a high blood glucose level has been artificially produced by injection of alloxan). It is possible, therefore, that saudin operates by a different mechanism than the hypoglycemic agents heretofore employed, and may for that reason find unique application in medicine. The results of comparative tests are given in the following Table 3, using mice injected intravenously with 50 mg/kg of alloxan 3 days before the tests.

While the present invention has been described by reference to certain specific operating steps, conditions, materials, techniques, and examples, it is to be understood that such details are illustrative only and are not intended to be limiting. Numerous variants thereof will be readily apparent to those of ordinary skill in the subject art without departing from the spirit of the invention.

I claim:

1. A compound of the formula

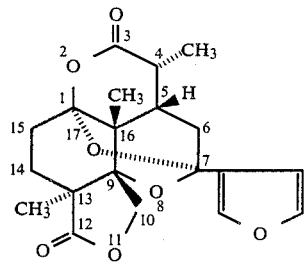

in substantially pure form.

2. A method for lowering blood sugar in an animal or human which method comprises parenteral administration to said animal or human of an effective amount of a compound of the formula

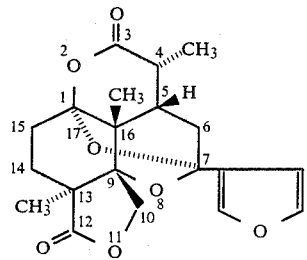

TABLE 3

EFFECT OF SAUDIN AND TOLBUTAMIDE ON BLOOD SUGAR LEVEL OF FASTING MICE
Blood Sugar Level, mg %, mean S.E.

| | Test Time, Hour | | | | | |
|---|---|---|---|---|---|---|
| | 0 | 1 | 2 | 3 | 4 | 5 |
| Control | 230 ± 40 | 327 ± 46 | 360 ± 50 | 355 ± 48.5 | 378 ± 51.5 | 377 ± 57.5 |
| No. mice | 7 | 7 | 7 | 7 | 7 | 6 |
| Saudin, injection, 40 mg/kg | 222 ± 25 | 288 ± 48.5 | 346 ± 55.4 | 342 ± 55.4 | 355 ± 54.3 | 443 ± 62.7 |
| No mice | 8 | 8 | 8 | 8 | 8 | 7 |
| Tolbutamide, inj., 150 mg/kg | 234 ± 51.4 | 185 ± 36 | 212 ± 40.4 | 235 ± 40.8 | 262 ± 54 | 347 ± 64 |
| No. mice | 5 | 6 | 6 | 6 | 6 | 6 | in a tissue-compatible liquid.

3. The method of claim 2 wherein between about 25 and about 100 mg/kg of the compound is administered in a tissue-compatible aqueous medium.

4. The method of claim 3 wherein said aqueous medium is normal saline.

5. The method of claim 3 wherein said aqueous medium is aqueous carboxymethylcellulose.

* * * * *